United States Patent
Cenci et al.

(10) Patent No.: US 10,679,599 B2
(45) Date of Patent: *Jun. 9, 2020

(54) SYSTEMS, APPARATUSES AND METHODS FOR ADAPTIVE NOISE REDUCTION

(71) Applicant: Empatica Srl, Milan (IT)

(72) Inventors: Ivan Cenci, Verucchio (IT); Simone Tognetti, Vimodrone (IT)

(73) Assignee: Empatica Srl, Milan (IT)

(*) Notice: Subject to any disclaimer, the term of this patent is extended or adjusted under 35 U.S.C. 154(b) by 0 days.

This patent is subject to a terminal disclaimer.

(21) Appl. No.: 16/161,897

(22) Filed: Oct. 16, 2018

(65) Prior Publication Data
US 2019/0259368 A1    Aug. 22, 2019

Related U.S. Application Data

(63) Continuation of application No. 14/688,621, filed on Apr. 16, 2015, now Pat. No. 10,134,378.

(Continued)

(51) Int. Cl.
| | | |
|---|---|---|
| *G10K 11/175* | (2006.01) | |
| *A61B 5/00* | (2006.01) | |
| *A61B 5/026* | (2006.01) | |
| *H03H 21/00* | (2006.01) | |
| *H03H 17/02* | (2006.01) | |

(52) U.S. Cl.
CPC .......... *G10K 11/175* (2013.01); *A61B 5/0261* (2013.01); *A61B 5/721* (2013.01); *A61B 5/725* (2013.01); *H03H 21/0012* (2013.01); *G10K 2210/3012* (2013.01);
(Continued)

(58) Field of Classification Search
CPC ......... G10K 11/175; G10K 2210/3012; G10K 2210/30232; G10K 2210/3028; A61B 5/0261; A61B 5/721; A61B 5/725; H03H 21/0012; H03H 17/0255; H03H 17/0257

USPC ...... 381/71.11, 71.8, 71.1, 71.9, 71.12, 94.1, 381/67; 701/536; 702/54, 141, 127; 700/94

See application file for complete search history.

(56) References Cited

U.S. PATENT DOCUMENTS 10,134,378 B1    11/2018 Cenci et al.

OTHER PUBLICATIONS

Non-Final Office Action dated Sep. 23, 2016 for U.S. Appl. No. 14/688,621, 17 pages.
(Continued)

*Primary Examiner* — Vivian C Chin
*Assistant Examiner* — Con P Tran
(74) *Attorney, Agent, or Firm* — Cooley LLP

(57) ABSTRACT

An apparatus includes a sensor module configured for receiving sensed information indicative of a sensed signal. The sensed signal includes a source signal component and a source noise component. The apparatus also includes a reference module configured for reference information indicative of a reference signal. The reference signal also includes a reference noise component. The apparatus also includes a filter module configured as a fixed lag Kalman smoother. The filter module is configured for adaptively filtering the reference signal to generate an estimate of the source noise component. The apparatus also includes a processing module configured for calculating an output signal based on the sensed signal and the estimate of the source noise component. The apparatus also includes an interface module configured for transmitting an indication of the output signal. The filter module is further configured for, based on the output signal, tuning the Kalman smoother.

18 Claims, 5 Drawing Sheets

Related U.S. Application Data

(60) Provisional application No. 61/980,044, filed on Apr. 16, 2014.

(52) U.S. Cl.
CPC ............... *G10K 2210/3028* (2013.01); *G10K 2210/30232* (2013.01); *H03H 17/0255* (2013.01); *H03H 17/0257* (2013.01)

(56) References Cited

OTHER PUBLICATIONS

Final Office Action dated Jun. 26, 2017 for U.S. Appl. No. 14/688,621, 26 pages.
Non-Final Office Action dated Jan. 4, 2018 for U.S. Appl. No. 14/688,621, 20 pages.

Receiving sensed information indicative of a sensed signal, the sensed signal including a source signal component and a source noise component
310

Receiving reference information indicative of a reference signal, the reference signal including a reference noise component
320

Adaptively filtering the reference signal to generate an estimate of the source noise component using a modified Kalman filter
330

Calculating an output signal associated with the source signal component, the output signal based on the sensed signal and the estimate of the source noise component
340

Transmitting an indication of the output signal
350 based on the output signal, tuning at least one aspect of the modified Kalman filter
360

SYSTEMS, APPARATUSES AND METHODS FOR ADAPTIVE NOISE REDUCTION

CROSS REFERENCE TO RELATED APPLICATIONS

This application is a continuation of U.S. patent application Ser. No. 14/688,621 filed Apr. 16, 2015, entitled "SYSTEMS, APPARATUSES AND METHODS FOR ADAPTIVE NOISE REDUCTION," which claims priority to, and the benefit of, U.S. Provisional Application Ser. No. 61/980,044, filed Apr. 16, 2014, entitled "METHOD FOR OPTIMIZED ADAPTIVE NOISE REDUCTION FROM PHOTOPLETHYSMOGRAPHIC SIGNAL," the entire disclosures of which are incorporated herein by reference in their entirety.

BACKGROUND

Adaptive noise canceling is a method for estimating the true value/nature of signals that are corrupted by additive noise or interference. In some approaches, a "primary" input $s=s+n_0$ is the corrupted signal, and a "reference" input $n_1$ containing noise correlated in some unknown way with the primary noise $n_0$ is a reference signal. The reference input can be adaptively filtered through a finite impulse response (FIR) structure/filter that is defined by a weight column vector w. The filter output can be subtracted from the primary input to obtain the signal estimate. In this manner, adaptive filtering before subtraction can allow for the treatment of inputs that are deterministic or stochastic, stationary or time variable.

Many adaptive techniques have been proposed, such as least mean squares and its variations normalized least mean squares, recursive least squares and variable step least mean squares. Recently, Kalman filters has been employed for this purpose, including, conventional Kalman filtering, fixed-lag smoothing and fixed-interval smoothing. Lee et al. (Physiol. Meas. 31 (2010), 1585-1603) demonstrated a Kalman smoother for eliminating motion artifacts from a photoplethysmography signal. Existing approaches, however, suffer from limited adaptivity and lag error.

Thus, a need exists for systems, apparatuses and methods for adaptive noise reduction with enhanced adaptivity and reduced/no lag error.

SUMMARY

An apparatus includes a sensor module configured for receiving sensed information indicative of a sensed signal. The sensed signal includes a source signal component and a source noise component. The apparatus also includes a reference module configured for reference information indicative of a reference signal. The reference signal also includes a reference noise component, the reference noise component associated with the source noise component. The apparatus also includes a filter module configured as a fixed lag Kalman smoother. The filter module is configured for adaptively filtering the reference signal to generate an estimate of the source noise component, including: setting the state noise covariance matrix to be the same as the measurement noise of the filter; setting the observation matrix to be the same as the reference signal; and setting the oblivion coefficient to be about one. The apparatus also includes a processing module configured for calculating an output signal associated with the source signal component, the output signal based on the sensed signal and the estimate of the source noise component. The apparatus also includes an interface module configured for transmitting an indication of the output signal. The filter module is further configured for based on the output signal, tuning at least one of the following aspects of the fixed lag Kalman smoother: the state noise covariance; the oblivion coefficient; or an order of the fixed lag Kalman smoother.

BRIEF DESCRIPTION OF THE DRAWINGS

FIG. 3 is a method for adaptive noise reduction, according to an embodiment.

DETAILED DESCRIPTION

In some embodiments, systems, apparatuses and methods for adaptive noise reduction are disclosed herein. Aspects disclosed herein adaptively remove noise from a corrupted input/source/primary signal when a reference input that is correlated with the source of noise is available. In an example case where the primary signal is a photoplethysmographic signal associated with the user, the reference input can be a secondary wavelength signal, or the output of an accelerometer associated with the user, and/or the like. When input signals have sharp spikes, discontinuities, and/ or are generally non-stationary (e.g., most physiological signals), aspects of the adaptive approach(es) disclosed herein can avoid undesired patterns that typically occur due to prior art approaches that fail to account for the non-stationary nature.

In some embodiments, a method includes receiving, at a processor of a computing device, sensed information indicative of a sensed signal. The sensed signal includes a source signal component and a source noise component. The method also includes receiving, at the processor, reference information indicative of a reference signal. The reference signal includes a reference noise component, the reference noise component associated with the source noise component. The method also includes adaptively filtering the reference signal to generate an estimate of the source noise component using a fixed lag Kalman smoother. The adaptive filtering includes setting the state noise covariance matrix to be the same as the measurement noise of the filter, setting the observation matrix to be the same as the reference signal, and setting the oblivion coefficient to be about one. The method also includes calculating an output signal associated with the source signal component. The output signal is based on the sensed signal and the estimate of the source noise component. The method also includes transmitting an indication of the output signal. The method also includes based on the output signal, tuning at least one of the following aspects of the fixed lag Kalman smoother: the state noise covariance, the oblivion coefficient, or an order of the fixed lag Kalman smoother.

Figure 1:
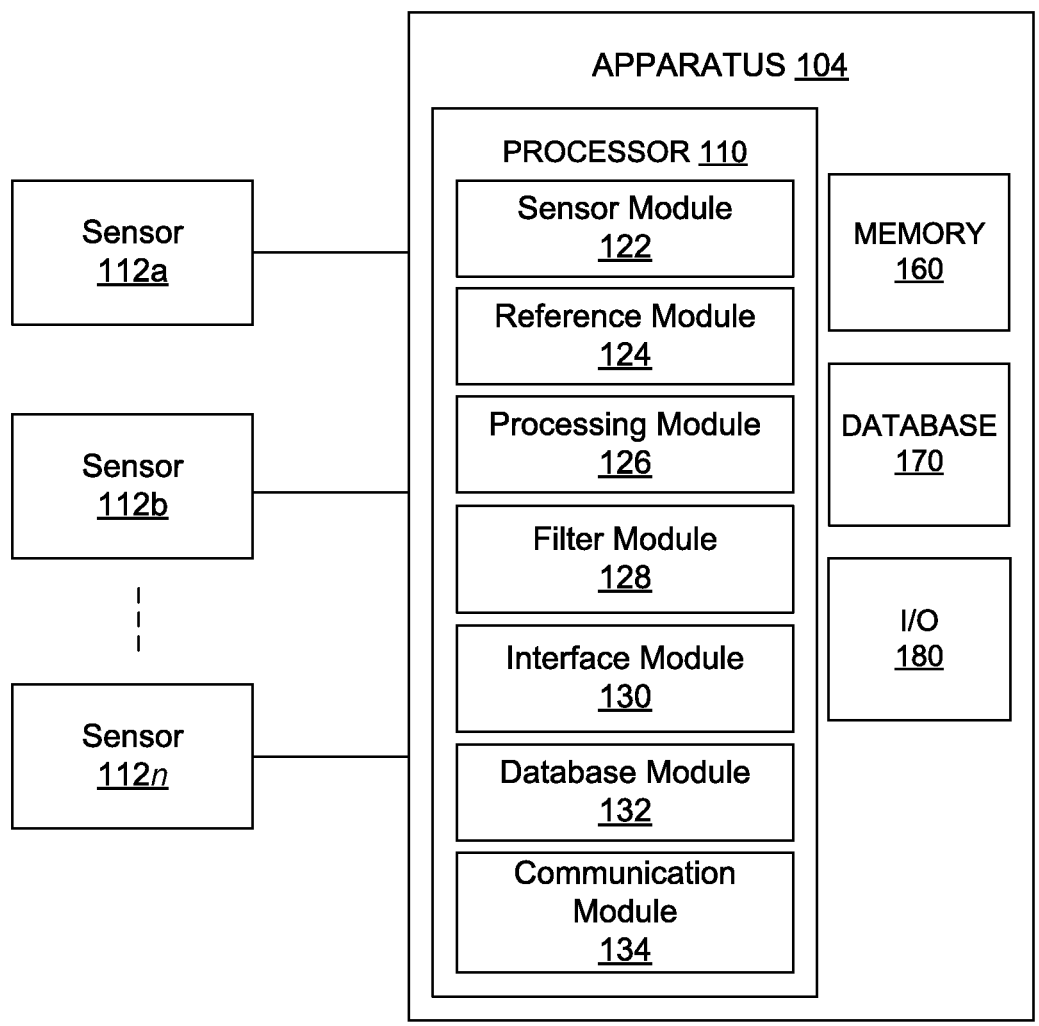
FIG. 1 is an illustration of a system, according to an embodiment.

FIG. 1 is a schematic illustration of a system 100 within which aspects of a system for adaptive noise can be implemented. The system 100 includes a set of sensors 112a-112n, and an apparatus 104. In some embodiments, at least one of the sensors 112a-112n is a source sensor, and at least another of the sensors 112a-112n is a reference sensor.

In some embodiments, the set of sensors 112a-112n can be any suitable sensors for generating sensed information associated with a user during use such as, for example, physiological information, activity information, geospatial information, and/or the like. Non-limiting examples of such sensed parameters can include heart and/or pulse rate, blood pressure, muscle electrical potential, nerve electrical potential, temperature, brain waves, motion, measures of activity, number of steps taken, location, acceleration, pace, distance, altitude, direction, velocity, speed, time elapsed, time left, and/or the like. The sensors 112a-112n can include, but are not limited to, electrodermal activity sensors, accelerometers, skin temperature sensors, ambient temperature sensors, gyroscopes, global positioning system (GPS) sensors, electrical sensors, conductance sensors, magnetometers, capacitive sensors, optical sensors, barometer sensors, respiration sensors, blood pressure sensors, humidity sensors, a camera, and/or the like. In some embodiments, the sensors 112a-112n at least include a photoplethysmographic sensor configured for capturing photoplethysmographic information. In some embodiments, at least one of the sensors 112a-112n is a source sensor, and at least another of the sensors 112a-112n is a reference sensor. In some embodiments, the sensors 112a-112n at least include a photoplethysmographic sensor as a source sensor configured for generating a photoplethysmographic signal (e.g., when the apparatus 104 and/or the system 100 is associated with a user), and an accelerometer as a reference sensor configured for generating a reference signal. In some embodiments, the sensors 112a-112n can include, as a reference sensor, one or more photodiode(s). As an example, the reference sensor can include 2 photodiodes connected in parallel, one for sensing red light and one for green light (e.g., from any suitable light source, such as LEDs). The red and green lights can be turned on and off alternatively for (for example) hundreds of microseconds every 1/64 seconds. An example cycle can be Green on >100 us—green off—red on >100 us—red off. In some embodiments, the sensors 112a-112n can include, as a reference sensor, a gyroscope. In some embodiments, at least one of the sensors 112a-112n can include a processor and/or a memory (not shown in FIG. 1).

Figure 2:
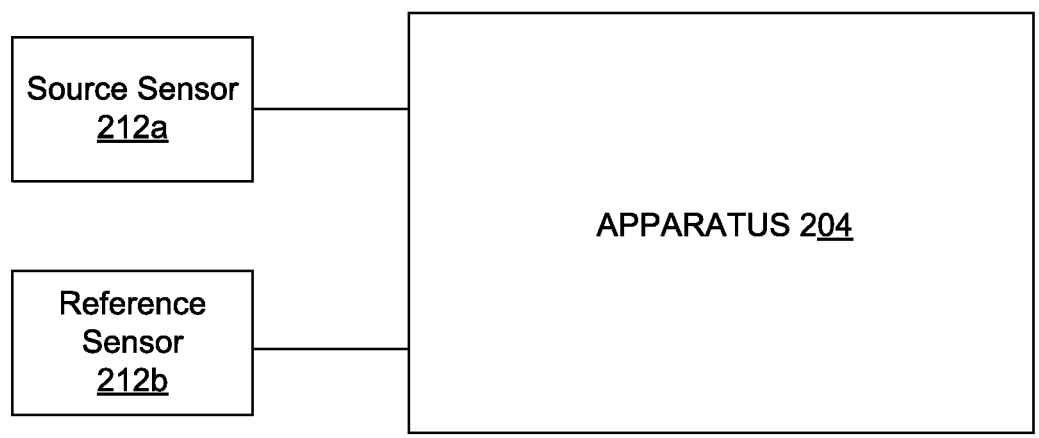
FIG. 2 is one embodiment of the system of FIG. 1.

FIG. 2 illustrates, for simplicity of explanation, an example system 200 (which can be structurally and/or functionally similar to the system 100) including an apparatus 204 (which can be structurally and/or functionally similar to the apparatus 204), a source sensor 212a (e.g., similar to the sensor 112a) and a reference sensor 212b (e.g., similar to the sensor 112b). In some embodiments, the source sensor 212a can be a photoplethysmographic sensor, and the reference sensor 212b can be an accelerometer.

Referring again to FIG. 1, the sensors 112a-112n can communicate with the apparatus 104, as indicated by solid lines in FIG. 1, via any suitable means, including wired and/or wireless (e.g., Wi-Fi, Bluetooth, NFC, optical, magnetic coupling, and/or the like) means. Although shown here as functionally distinct from the apparatus 104, is understood that, in some embodiments, each of the sensors 112a-112n can be (independently) structurally connected and/or integrated with the apparatus 104. In some embodiments, the sensors 112a-112n can be formed as wearable sensors, such as on a wristband, and the apparatus 104 can be a smartphone. In some embodiments (not shown), two or more of the sensors 112a-112n can be in communication with each other.

In some embodiments, the apparatus 104 can be in communication with the sensors 112a-112n and/or other devices (not shown) via, for example, one or more networks, each of which can be any type of network such as, for example, a local area network (LAN), a wide area network (WAN), a virtual network, a telecommunications network, and/or the Internet, implemented as a wired network and/or a wireless network. Any or all communications can be secured (e.g., encrypted) or unsecured, as is known in the art. The apparatus 104 can be a personal computer, a server, a work station, a tablet, a mobile device, a cloud computing environment, an application or a module running on any of these platforms, and/or the like.

In some embodiments, aspects of the system 100 are operable for heartbeat detection, such as generally disclosed in PCT Application Publication No. WO2014/115075 entitled "DEVICE, SYSTEM, AND METHOD FOR DETECTION AND PROCESSING OF HEARTBEAT SIGNALS", with an international filing date of Jan. 21, 2014, the entire disclosure of which is incorporated herein by reference. In some embodiments, aspects of the system 100 are operable for measuring electrodermal activity, such as generally disclosed in U.S. application Publication Ser. No. 14/215,613 entitled "APPARATUS FOR ELECTRODERMAL ACTIVITY MEASUREMENT WITH CURRENT COMPENSATION", filed Mar. 17, 2014, the entire disclosure of which is incorporated herein by reference. In some embodiments, aspects of the system 100 are operable for monitoring well being, such as generally disclosed in U.S. application Publication Ser. No. 14/684,933 entitled "SYSTEMS, APPARATUSES, AND METHODS FOR MONITORING WELL BEING", filed Apr. 11, 2015, the entire disclosure of which is incorporated herein by reference.

The apparatus 104 includes at least a processor 110 and a memory 160. FIG. 1 also illustrates a database 170, although it will be understood that, in some embodiments, the database 170 and the memory 160 can be a common data store. In some embodiments, the database 170 constitutes one or more databases. Further, in other embodiments (not shown), at least one database can be external to the apparatus 104 and/or the system 100. FIG. 1 also illustrates an input/output (I/O) component 180, which can depict one or more input/output interfaces, implemented in software and/or hardware, for the sensors 112a-112n, and/or other entities to interact directly or indirectly with the system 100. As an example, the I/O 180 can be used for tuning the operation of an adaptive filter (discussed in detail later) of the apparatus 104.

The memory 160 and/or the database 170 can independently be, for example, a random access memory (RAM), a memory buffer, a hard drive, a database, an erasable programmable read-only memory (EPROM), an electrically erasable read-only memory (EEPROM), a read-only memory (ROM), Flash memory, and/or so forth. The memory 160 and/or the database 170 can store instructions to cause the processor 110 to execute modules, processes and/or functions associated with the system 100.

The processor 110 includes a sensor module 122, a reference module 124, a filter module 126, a processing module 128, an interface module 130, a database module 132, and a communication module 134. In some embodiments, the processor 110 can include additional modules (not shown). Each module can independently be a hardware module and/or a software module (implemented in hardware, such as the processor 110).

In some embodiments, the functionality of one or more of the modules can be combined and/or overlap. For example, the communication module 134 and the database module 132 can be a single module. As another example, the sensor module 122 and the reference module 124 can be a single module. In some embodiments, the functionality of one or more modules and/or the interaction between the modules can be based on regulatory requirements for data processing, storage, integrity, security, and/or the like.

While shown as being implemented in processor 110, in other embodiments, the modules can be distributed. In such embodiments, for example, the filter module 128 can be at a first processor and/or network device and the database module 132 can be at a second processor and/or network device. Such processors and/or network devices can be communicatively coupled via, for example, a network.

The processor 110 can be any suitable processing device configured to run and/or execute a set of instructions or code. The processor 110 can be, for example, a general purpose processor, a Field Programmable Gate Array (FPGA), an Application Specific Integrated Circuit (ASIC), a Digital Signal Processor (DSP), and/or the like. The processor 110 can be configured to run and/or execute application processes and/or other modules, processes and/or functions associated with the device 100 and/or the network.

The communication module 134 can be configured to facilitate network connectivity for the apparatus 104 and/or the system 100. For example, the communication module 134 can include and/or enable a network interface controller (NIC), wireless connection, a wired port, and/or the like. As such, the communication module 134 can establish and/or maintain a communication session with the sensors 112a-112n. Similarly stated, the communication module 140 can enable the system 100 to send data (e.g., control signals) to and/or receive data (e.g., sensed information) from the sensors 112a-112n.

The database module 132 is configured for interfacing with the memory 160 and/or the database 170 for data manipulation (including storage, modification, and/or deletion). For example, the database module 132 can be operable for storing the sensed information and/or the reference information (e.g., received from the sensors 112a-112n) in the memory 160 and/or the database 170.

The sensor module 122 is configured to communicate with the sensors 112a-112n, such as to receive sensed information from the sensors 112a-112n, to control operation of the sensors 112a-112n, and/or the like. In some embodiments, the sensor module 122 is configured for receiving sensed information indicative of a sensed signal. In some embodiments, the sensed signal s(k) includes a source signal component s(k) and a source noise component $n_0(k)$. In some embodiments, the sensed signal can be represented based on a state-space representation of apparatus 104 and/or any subpart thereof, such as, for example, the processor 110 and/or the filter module 126, that receives the sensed signals and generates output signals (described hereon using the apparatus 104, for simplicity). The state-space representation can be expressed by Eqs. 1 and 2:

$$x_k = A_{k-1} x_{k-1} + n_{k-1} \quad (1)$$

$$y_k = C_k x_k + e_k \quad (2)$$

where Eq. 1 is a state equation, and Eq. 2 is an observation equation corresponding to the sensed signal. Generally, a state-space representation can be considered a representation of a physical system (e.g., the system 100 and/or the apparatus 104) as a set of related input, output and state variables. The state of such a system can be of interest, and dependent on past inputs and/or states. The output of such a system (such as acceleration, for example), is measureable, such as via a sensor. As an example, speed can be estimated using such a state-space representation when the input variable is acceleration.

Here, $x_k$ is the state vector of the apparatus 104, $A_k$ is a transition matrix, $C_k$ is an observation matrix and $y_k$ is the sensed information (also referred to as "observation data") at time/sample "k". $n_k$ is a system noise vector and $e_k$ is the observation noise. In some embodiments, both $n_k$ and $e_k$ can be assumed to be zero-mean white Gaussian noise processes, respectively, e.g., $n_k \sim N(0, Q_k)$ and $e_k \sim N(0, \sigma_k^2)$, and to be independent of each other. $Q_k$ is the state noise covariance matrix, $\sigma_k^2$ is the measurement noise variance, and N is a stochastic signal represented as (mean, variance) and having normal or Gaussian distribution. In some embodiments, the state vector can be expressed as a random walk model, such that the state transition matrix $A_k$ becomes the identity matrix, and the state vector $x_k$ can be represented as shown in Eq. 3:

$$x_k = x_{k-1} + n_{k-1} \quad (3)$$

In some embodiments, the sensed information received from the sensors 112a-112n can include, but is not limited to, one or more of raw sensor signal information, processed sensor signal information, timestamp information, time window information, contextual information, and/or the like. In some embodiments, the sensed information can indicate a time period during which the sensed information was obtained/collected. In some embodiments, the sensed information is stored in the memory 160 and/or the database 170, and the sensor module 122 is configured to receive the stored sensed information, such as, for example, via the database module 132.

The reference module 124 is configured for receiving reference information indicative of a reference signal. In some embodiments, the reference signal including a reference noise component, the reference noise component associated with the source noise component. The reference noise component can be any signal that is correlated with the noise source, such as motion. For example, a green signal (described earlier) can be sensed to represent noise due to heart rate and/or motion. In some embodiments, the reference information is obtained via one of the sensors 112a-112n, and the reference module 124 is configured to obtain the reference information either directly from the sensors 112a-112n and/or via the sensor module 122. In some embodiments, the reference information is stored in the memory 160 and/or the database 170, and the reference module 124 is configured to receive the stored reference information, such as, for example, via the database module 132.

The filter module 126 is configured for receiving the reference information from the reference module 124, and is further configured for adaptively filtering the reference signal to generate an estimate of the source noise component of the source signal. In some embodiments, the filter module 126 is configured as a Kalman filter. For a general description of Kalman filters, see at least chapter 5 of "Optimal State Estimation: Kalman, H Infinity, and Nonlinear Approaches" by Dan Simon (ISBN: 978-0471708582), the entire book disclosure of which is incorporated herein by reference in its entirety.

In some embodiments, the filter module 126 is configured as a fixed lag Kalman smoother, as explained further herein.

The following Referring to Eqs. 1-3, the Kalman equations for the Kalman filter/smoother can be derived as Eqs. 3-5:

$$P_k = \mu(I - K_k C_k)P_{k-1}Q_k \quad (3)$$

$$K_k = P_{k-1}C_k{}^t(C_k P_{k-1} C_k{}^t + \sigma_k^2)^{-1} \quad (4)$$

$$\hat{x}_k = \hat{x}_{k-1} + K_k(y_k - C_k \hat{x}_{k-1}) \quad (5)$$

where $K_k$ is the gain of the Kalman smoother, and can depend on how much the Kalman smoother is perturbed/disturbed (see parameter $P_k$), as well as how much the sensed signal $\sigma_k^2$ (e.g., photoplethysmography signal, accelerometer signal, and/or the like) is perturbed/disturbed. $\mu$ is an oblivion coefficient that can be tuned to enhance the responsiveness of the system 100 to subsequently received data, such as new source information. $x_k$ is a state vector estimate, and $P_k$ is the covariance matrix of the state estimate error. The gain $K_k$ can be used to update the state estimate $x_k$ when a new observation, such as new source information, is detected and/or received. As an illustrative example of the interaction of these variables, if $P_k$ is relatively greater than $\sigma_k^2$, then $K_k$ tends to be closer to a value of 1, and considers the observation $y_k$ to be relatively more accurate. On the other hand, if $\sigma_k^2$ is relatively greater than $P_k$, then $K_k$ tends to be closer to a value fo 0, and considers the $\sigma_k^2$ to be relatively more accurate.

In some embodiments, the filter module 126 is configured such that the order N of the Kalman smoother is an even number. In this manner, a moving average window (of length N+1) of the source signal can be centered in the $k^{th}$ sample, permitting use of information contained in "future" data (i.e., data received after the $k^{th}$ sample). This approach avoids lag error while introducing a delay of N/2 taps or samples between (a) the source signal s, and the reference signal $n_1$, and (b) the output signal, resulting in a "fixed lag" Kalman filter/smoother. Said another way, the output signal will lag N/2 samples behind the input at any point of time.

In some embodiments, the filter module 126 is configured for setting the observation data $y_k$ to be the same as the source signal $\tilde{s}(k) = s(k) + n_0(k)$. In some embodiments, the filter module 126 is further configured for setting the observation matrix $C_k$ to be the same as the reference signal (referred to as "$n_1(k)$" or "$n_1$" in the equations below). In some embodiments, the filter module 126 is further configured for setting the oblivion coefficient $\mu$ to be less than or equal to about one. Substituting in Eqs. 3-5, we obtain Eqs. 6-8:

$$P_k = \mu(I - K_k n_1{}^T)P_{k-1}Q_k \quad (6)$$

$$K_k = P_{k-1}n_1(k)/(n_1^T(k)P_{k-1}n_1(k) + \sigma_k^2)^{-1} \quad (7)$$

$$\hat{w}(k) = \hat{w}(k-1) + K_k(\tilde{s}(k) - n_1^T(k)\hat{w}(k-1)) \quad (8)$$

Where $\hat{w}(k)$ are tap-weight estimates (i.e., the weighting value(s) employed by the Kalman Smoother) that correspond to the state vector estimates $x_k$ in some embodiments. The tap-weight estimates are updated, for each sample k, based the Kalman gain $K_k$ to provide the best possible estimate of the source noise component y. In some embodiments, the filter module 126 is configured for generating the estimate of the source noise component y based on a convolution operation between (1) the reference signal $n_1(k)$ and (2) either the state vector estimate $x_k$ or the tap weight estimate $\hat{w}(k)$.

The processing module 128 is configured for calculating an output signal (also referred to as "z") associated with the source signal component. The output signal is based on the sensed signals and the estimate of the source noise component y. The processing module 128 is configured for calculating the output signal in any suitable manner including, but not limited to, addition, weighted addition, subtraction, weighted subtraction, and/or the like.

The interface module 132 is configured for transmitting an indication of the output signal z, such as, for example, to a display device (not shown) associated with the apparatus 104, to a third party device (not shown), and/or the like. In some embodiments, the interface module 132 and/or the processing module 128 is configured to transmit an indication of the output signal z to the filter module 126, such as, for example, the output signal itself, an error indicator associated with the output signal (e.g., a measure of the accuracy of the estimate of the source noise component y), and/or the like.

Referring again to the filter module 126, in some embodiments, the filter module 126 is configured to represent the state noise covariance matrix $Q_k$ as $Q_k = \sigma_{kf}^2 I$, where $\sigma_{kf}^2$ is the state noise variance and I is the identity matrix. In some embodiments, the measurement noise variance $\sigma_k^2$ can be set to 1.

In some embodiments, the filter module 126 is further configured for, based on the indication of the output signal received from the interface module 132 and/or the processing module 128, tuning and/or modifying one or more operating parameters of the fixed-lag Kalman smoother. In some embodiments, the filter module 126 is further configured for tuning/modifying the state noise covariance $\sigma_{kf}^2$ of the Kalman smoother. In some embodiments, the filter module 126 can tune/modify the state noise covariance $\sigma_{kf}^2$ based on one or more criterion associated with the sensed signal sensed signal $\tilde{s}$ and the reference signal $n_1$. In some embodiments, when at least one of (a) the sensed signal exceeds a sensed signal threshold, or (b) the reference signal exceeds a reference signal threshold, the filter module 126 is configured to increment the state noise covariance $\sigma_{kf}^2$ up to a maximum state noise covariance threshold. In some embodiments, this incremental approach is performed in a stepwise manner based on a state noise covariance increment, which can be predetermined/prespecified. In some embodiments, when (c) the sensed signal is below the sensed signal threshold, and (d) the reference signal is below the reference signal threshold, the filter module 126 is configured to decrement the state noise covariance, such as back to an original value, in a stepwise manner based on the state noise covariance increment. In this manner, sudden fluctuations in the source signal and/or the reference signal can be attenuated in the output signal by imposing a more gradual increase/decrease in state noise covariance.

In some embodiments, the interface module 132 is configured for receiving user input for modifying at least one of the sensed signal threshold, the reference signal threshold, the state noise covariance threshold, or the state noise covariance increment. In this manner, the adaptiveness/responsiveness of the filter module 126 can be tweaked. In some embodiments, the filter module 126 is configured to modify at least one of the sensed signal threshold, the reference signal threshold, the state noise covariance threshold, or the state noise covariance increment.

In some embodiments, the filter module 126 is further configured for tuning/modifying, and/or permitting (user input for) tuning/modification of, the oblivion coefficient $\mu$ of the Kalman smoother. In some embodiments, the filter module 126 is further configured for tuning/modifying, and/or permitting (user input for) tuning/modification of, the order N of the Kalman smoother. In this manner, the lag of the fixed-lag Kalman smoother of the filter module 126 can be controlled.

As described herein, in some embodiments, the memory 160 and/or the database 170 can store the source information and/or the reference information. In such embodiments, the filter module 126 can be further configured to calculate the state estimate $\hat{x}_k$ at the time point k (where k=1, ..., T time points of the source signal) of the time interval 1 ... T can be obtained given the source signal data $y_1, ..., y_T$. In some embodiments, the filter module 126 can additionally operate as a fixed-interval Kalman smoother, as illustrated by Eqs. 9-10:

$$K'_k = (P_k - Q_{k+1})(P_k)^{-1} \qquad (9)$$

$$\hat{w}'(k) = \hat{w}(k) + K'_k(\hat{w}'(k+1) - \hat{w}(k+1)) \qquad (10)$$

Where $K'_k$ is the Kalman gain for the fixed-interval Kalman smoother and $\hat{w}'(k)$ are the tap-weight estimates for the fixed-interval Kalman smoother.

Explained with reference to FIGS. 1-2, FIG. 3 illustrates a method 300 of adaptive noise reduction, according to an embodiment. The method 300 can be performed by the system 100 and/or the system 200, or any structural/functional equivalent thereof.

At 310, the method 300 includes receiving, at a processor (e.g., the processor 110), sensed information indicative of a sensed signal (e.g., a sensed signal from the source sensor 212*a*). The sensed signal includes a source signal component and a source noise component. In some embodiments, the sensed information includes photoplethysmographic information. The method 300 can further include sensing the photoplethysmographic information via a photoplethysmographic sensor.

At 320, the method 300 includes receiving, at the processor, reference information indicative of a reference signal (e.g., a sensed signal from the source sensor 212*b*). The reference signal including a reference noise component that is associated with the source noise component.

At 330, the method 300 includes adaptively filtering the reference signal to generate an estimate of the source noise component using a fixed lag Kalman smoother (e.g., via the filter module 126). In some embodiments, the order of the Kalman smoother is an even number. In some embodiments, adaptively filtering includes setting the observation data to be the same as the source signal. In some embodiments, adaptively filtering includes setting the observation matrix to be the same as the reference signal. In some embodiments, adaptively filtering includes setting the oblivion coefficient to be about one.

At 340, the method 300 includes calculating an output signal associated with the source signal component (e.g., via the processing module 128). The output signal is based on the sensed signal and the estimate of the source noise component. In some embodiments, calculating the output signal includes subtracting the estimate of the source noise component from the sensed signal to generate the output signal.

At 350, the method 300 includes transmitting an indication of the output signal, such as to a user interface, to a third party device, and/or the like.

At 360, the method 300 includes, based on the output signal, tuning at least one of the following aspects of the Kalman smoother: the state noise covariance, the oblivion coefficient, or an order of the Kalman smoother. In some embodiments, tuning the Kalman smoother including tuning the state noise covariance. In some embodiments, tuning the state noise covariance includes, when at least one of (a) the sensed signal exceeds a sensed signal threshold, or (b) the reference signal exceeds a reference signal threshold, incrementing the state noise covariance up to a state noise covariance threshold based on a state noise covariance increment. In some embodiments, tuning the state noise covariance includes, when (c) the sensed signal is below the sensed signal threshold, and (d) the reference signal is below the reference signal threshold, decrementing the state noise covariance based on the state noise covariance increment. In some embodiments, the method 300 further includes modifying at least one of the sensed signal threshold, the reference signal threshold, the state noise covariance threshold, or the state noise covariance increment. In some embodiments, tuning the Kalman smoother includes tuning the oblivion coefficient, such as, for example, constraining the oblivion coefficient to be between zero and about one. In some embodiments, tuning the Kalman smoother includes tuning the order of the Kalman smoother.

Figure 4:
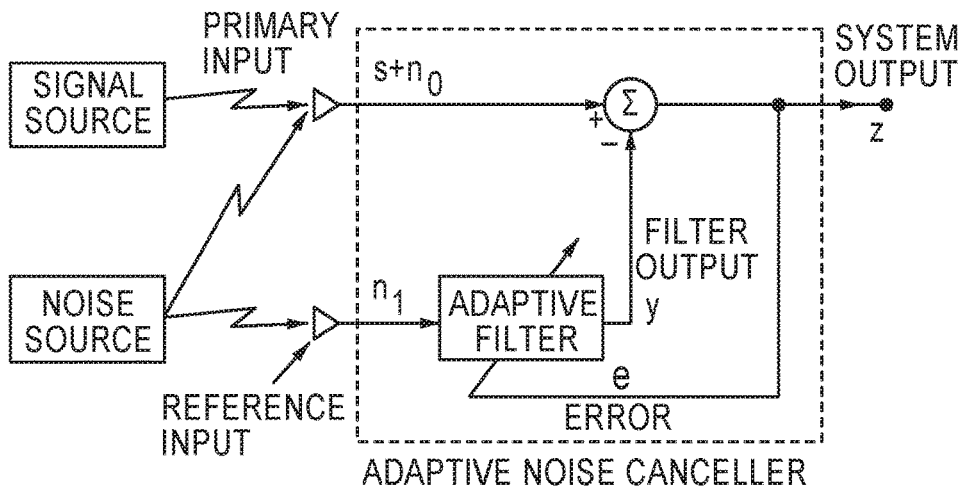
FIG. 4 is an illustration of an adaptive noise canceller, according to an embodiment.

FIG. 4 is an illustration of aspects of the systems, apparatuses, and method disclosed herein. A primary input (e.g., the sensor module 122) generates a source signal (designated by the term "s+$n_0$") based on input that includes a source component ("signal source") and a noise component (e.g., the source noise component). A reference input (e.g., the reference module 124) receives a reference input and an input from the noise source as well to generate a reference signal $n_1$. The noise in the reference signal, arising from the noise source, is correlated in some known/unknown way with the source noise component. A filter ("Adaptive Filter") associated with an adaptive noise canceller (e.g., a combination of the filter module 126 and the processing module 128) generates an output y that is an estimate of the source noise component. The estimate of the source noise component is subtracted from the source signal within the adaptive noise canceller to generate an output z that is an estimate of the source component. Some aspect of the output z, such as an error e, is fed back to the adaptive filter for tuning the filter.

Example 1

Figure 5:
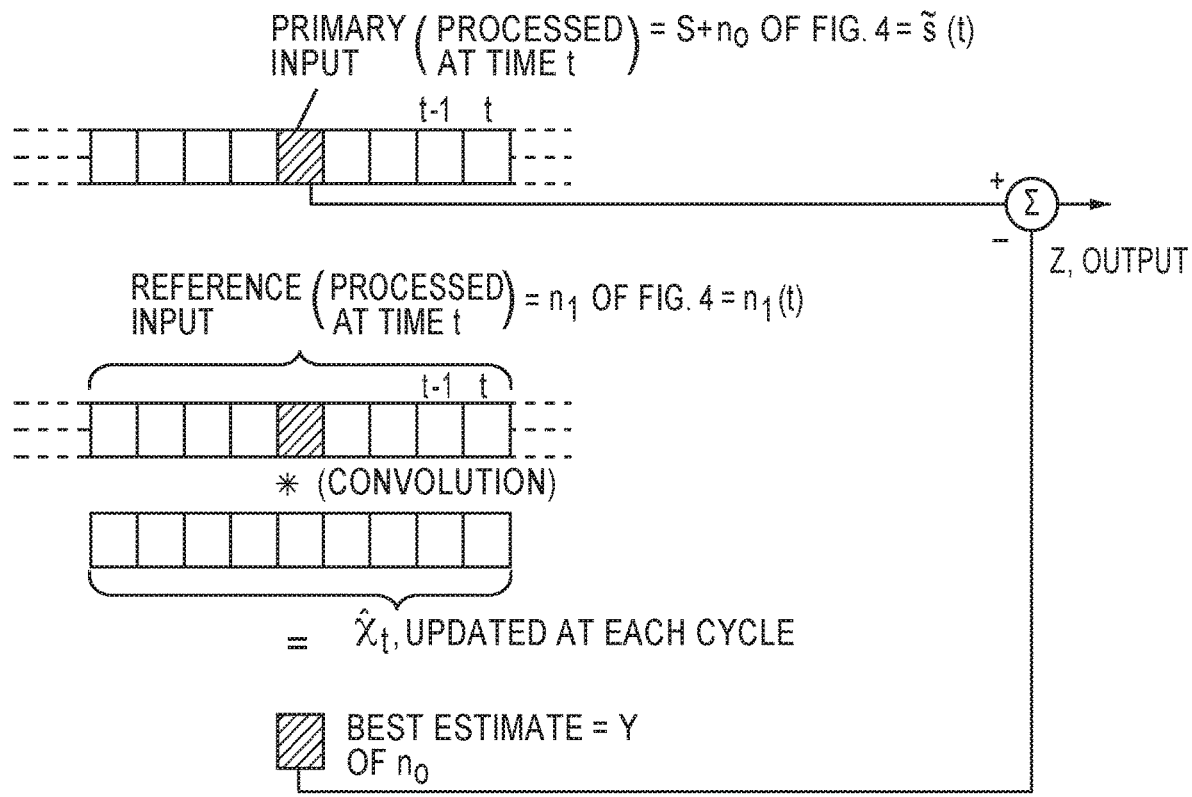
FIG. 5 is an example illustration of a fixed-lag Kalman smoothing approach.

FIG. 5 is an example illustration of a fixed-lag Kalman smoothing approach. A primary input signal (similar to $\tilde{s}(k)$) includes N+1 samples over times 1 ... t, and a sample time k in the middle is processed, in a fixed-lag manner. A reference input signal (similar to $n_1(k)$) is convolved with the state vector estimates $x_k$ (i.e., corresponding to the tap-weight estimates $\hat{w}(k)$) for the samples over times 1 ... t to generate the estimate y of the source noise component. The estimate y is subtracted from $\tilde{s}(k)$ to generate the output signal z.

The dimensions of $n_1(k)$ and $\hat{x}_k$ is N, and can be tuned, such as at the time of filter design (e.g., at the time of design of the filter module 126).

Example 2

Figure 6:
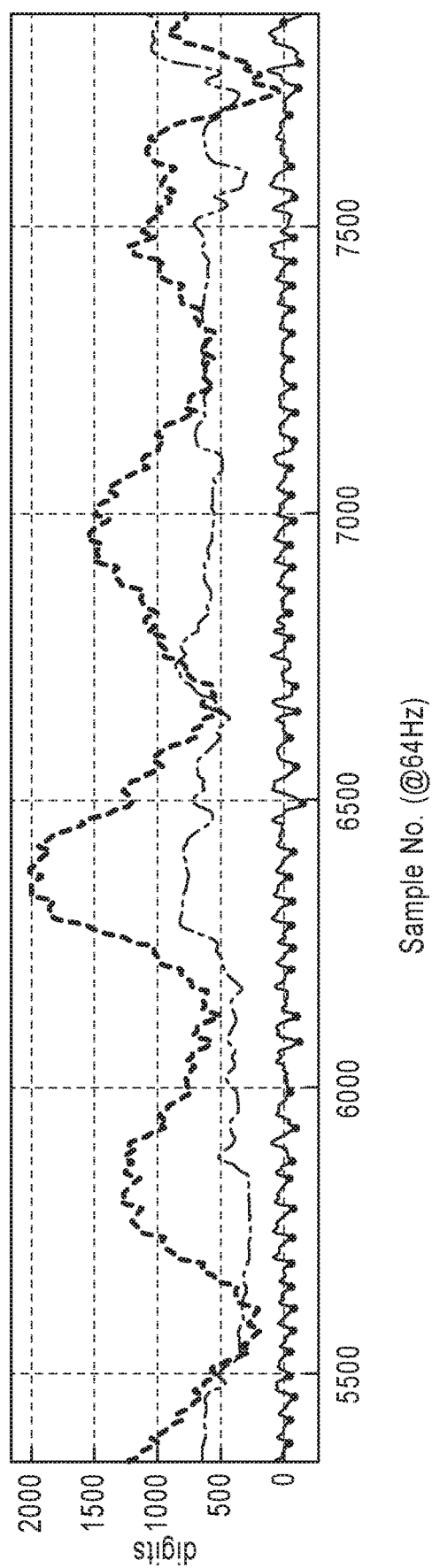
FIG. 6 is a example plot of a source signal, a reference signal, and an output signal derived therefrom.

FIG. 6 is an example plot illustrating a source signal (light dashed line), a reference signal (dark dashed line), and the resulting output signal (solid line). The source signal is a combined ECG reading of a pregnant woman and her fetus; the reference signal is the ECG of the pregnant woman alone; and the resulting output signal is an estimate of the heartbeat of the fetus alone. Block dots indicate diastolic notches, and can be used to determine heart rate of the fetus more accurately.

It is noted that while disclosed here using photoplethysmographic signals and/or red/green signals as examples, aspects disclosed herein are not limited thereto, and are applicable to any signal for which a reference signal with related noise can be obtained. Non-limiting examples of applications for the systems, apparatuses, and methods disclosed herein include, but are not limited to, electrocardiography (e.g., for removing 60 Hz noise, for removing donor ECG at heart transplant, for removing maternal ECG as described in Example 2), speech (e.g., removing noise such as ambient noise from speech signals), antenna design (e.g., eliminating antenna sidelobe interference), general removal of periodic interference (e.g., background hum in music recordings), and/or the like. Additional applications for use of the systems, apparatuses, and methods disclosed herein can be found in "Adaptive Noise Cancelling: Principles and Applications", Widrow et al, Proceedings of the IEEE, Vol. 63, No. 12, December 1975), the entire disclosure of which is incorporated herein by reference in its entirety.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, and/or files containing higher-level instructions that are executed by a computer using an interpreter. For example, embodiments may be implemented using C, Java, C++, MATLAB or other programming languages and/or other development tools.

The processors described herein can be any processors (e.g., a central processing unit (CPU), an application-specific integrated circuit (ASIC), and/or a field programmable gate array (FPGA)) configured to execute one or more instructions received from, for example, a memory. In some embodiments, at least one processor can be a Reduced Instruction Set computing (RISC) processor. Each processor can be in communication with a memory and/or a network card. In some embodiments, each processor can accordingly send information (e.g., data, instructions and/or network data packets) to and/or receive information from a memory and/or a network card.

The memory can be any memory (e.g., a RAM, a ROM, a hard disk drive, an optical drive, other removable media) configured to store information (e.g., one or more software applications, user account information, media, text, etc.). The memory can include one or more modules performing the functions described herein. In some embodiments, the functions described herein can be performed by any number of modules. For example, in some embodiments, the functions described herein can be performed by a single module.

While various embodiments have been described above, it should be understood that they have been presented by way of example, and not limitation. Where methods described above indicate certain events occurring in certain order, the ordering of certain events can be modified. Additionally, certain of the events may be performed concurrently in a parallel process when possible, as well as performed sequentially as described above.

What is claimed is:

1. An apparatus, comprising:
 a sensor module configured for receiving sensed information indicative of a sensed signal, the sensed signal including a source signal component and a source noise component;
 a reference module configured for receiving reference information indicative of a reference signal, the reference signal including a reference noise component, the reference noise component associated with the source noise component;
 a filter module configured as a fixed lag Kalman smoother, the filter module configured for adaptively filtering the reference signal to generate an estimate of the source noise component, including:
 setting the observation data to be the same as the source signal;
 setting the observation matrix to be the same as the reference signal; and
 setting the oblivion coefficient to be about one;
 a processing module configured for calculating an output signal associated with the source signal component, the output signal based on the sensed signal and the estimate of the source noise component; and
 an interface module configured for transmitting an indication of the output signal,
 the filter module further configured for, based on the output signal, tuning at least one of the following aspects of the Kalman smoother:
 the state noise covariance;
 the oblivion coefficient; or
 an order of the Kalman smoother.

2. The apparatus of claim 1, wherein the sensed information includes sensed photoplethysmographic information, further comprising a photoplethysmographic sensor configured for capturing the photoplethysmographic information.

3. The apparatus of claim 1, wherein the reference information includes accelerometer information, further comprising an accelerometer configured for capturing the reference information.

4. The apparatus of claim 1, the filter module configured to tune the Kalman smoother by modifying the state noise covariance, the filter module configured to modify the state noise covariance by:
 when at least one of (a) the sensed signal exceeds a sensed signal threshold, or (b) the reference signal exceeds a reference signal threshold, incrementing the state noise covariance up to a state noise covariance threshold based on a state noise covariance increment; and
 when (c) the sensed signal is below the sensed signal threshold, and (d) the reference signal is below the reference signal threshold, decrementing the state noise covariance based on the state noise covariance increment.

5. The apparatus of claim 4, the interface module further configured for modifying at least one of the sensed signal threshold, the reference signal threshold, the state noise covariance threshold, or the state noise covariance increment.

6. The apparatus of claim 1, the filter module configured to tune the Kalman smoother by modifying the oblivion coefficient.

7. The apparatus of claim 1, the filter module configured to tune the Kalman smoother by modifying the order of the Kalman smoother.

8. The apparatus of claim 1, the processing module configured to calculate the output signal by subtracting the estimate of the source noise component from the sensed signal to generate the output signal.

9. The apparatus of claim 1, further comprising:
a database storing the sensed information; and
a database module operably coupled to the database, the database module configured to communicating the sensed information from the database to the sensor module.

10. The apparatus of claim 1, further comprising:
a database storing the sensed information and the reference information; and
a database module operably coupled to the database, the database module configured for communicating the sensed information from the database to the sensor module, the database module further configured for communicating the reference information to the reference module.

11. A method, comprising:
receiving, at a processor, sensed information indicative of a sensed signal, the sensed signal including a source signal component and a source noise component;
receiving, at the processor, reference information indicative of a reference signal, the reference signal including a reference noise component, the reference noise component associated with the source noise component;
adaptively filtering the reference signal to generate an estimate of the source noise component using a fixed lag Kalman smoother, including:
setting the observation data to be the same as the source signal;
setting the observation matrix to be the same as the reference signal; and
setting the oblivion coefficient to be about one;
calculating an output signal associated with the source signal component, the output signal based on the sensed signal and the estimate of the source noise component;
transmitting an indication of the output signal; and
based on the output signal, tuning at least one of the following aspects of the Kalman smoother:
the state noise covariance;
the oblivion coefficient; or
an order of the Kalman smoother.

12. The method of claim 11, wherein the sensed information includes photoplethysmographic information, further comprising sensing the photoplethysmographic information via a photoplethysmographic sensor.

13. The method of claim 11, the tuning the Kalman smoother including modifying the state noise covariance, further comprising:
when at least one of (a) the sensed signal exceeds a sensed signal threshold, or (b) the reference signal exceeds a reference signal threshold, incrementing the state noise covariance up to a state noise covariance threshold based on a state noise covariance increment; and
when (c) the sensed signal is below the sensed signal threshold, and (d) the reference signal is below the reference signal threshold, decrementing the state noise covariance based on the state noise covariance increment.

14. The method of claim 13, further comprising modifying at least one of the sensed signal threshold, the reference signal threshold, the state noise covariance threshold, or the state noise covariance increment.

15. The method of claim 11, the tuning the Kalman smoother including modifying the oblivion coefficient.

16. The method of claim 11, the tuning the Kalman smoother including modifying the order of the Kalman smoother.

17. The method of claim 11, wherein the order of the Kalman smoother is an even number.

18. The method of claim 11, the calculating the output signal including subtracting the estimate of the source noise component from the sensed signal to generate the output signal.

* * * * *